United States Patent [19]

Heckle et al.

[11] Patent Number: 4,952,541
[45] Date of Patent: Aug. 28, 1990

[54] ACRYLONITRILE DIMERIZATION PROCESS AND METHOD OF TREATING RESIDUAL CATALYST

[75] Inventors: William A. Heckle; Marion J. Mathews, III, both of Pensacola, Fla.; P. Robert Peoples, St. Louis, Mo.

[73] Assignee: Monsanto Company, Pensacola, Fla.

[21] Appl. No.: 401,722

[22] Filed: Sep. 1, 1989

[51] Int. Cl.$^5$ ............................................. B01J 38/70
[52] U.S. Cl. ........................................ 502/22; 502/23; 502/32; 502/34; 502/38; 558/363
[58] Field of Search ............... 502/23, 22, 162, 32, 502/34, 38; 558/363

[56] References Cited

U.S. PATENT DOCUMENTS

| | | | |
|---|---|---|---|
| 3,800,000 | 3/1974 | Fahey | 502/162 |
| 4,089,890 | 5/1978 | Jennings et al. | 558/363 |
| 4,100,186 | 7/1978 | Wright | 558/363 |
| 4,102,915 | 5/1977 | Jennings et al. | 260/465.8 |
| 4,126,632 | 11/1978 | Hogan et al. | 260/465.8 |
| 4,138,428 | 2/1979 | Jennings et al. | 260/465.8 |
| 4,574,060 | 3/1986 | Boyle et al. | 558/457 |
| 4,639,539 | 1/1987 | Hovey et al. | 558/363 |
| 4,661,615 | 4/1987 | Boyle et al. | 558/363 |
| 4,841,087 | 6/1989 | Mathews et al. | 558/363 |

*Primary Examiner*—Anthony McFarlane
*Attorney, Agent, or Firm*—Thomas N. Wallin

[57] ABSTRACT

Treatment of dicyanobutene to inactivate residual dimerization catalyst facilitates hydrogenation of the product to form adiponitrile.

4 Claims, No Drawings

ACRYLONITRILE DIMERIZATION PROCESS AND METHOD OF TREATING RESIDUAL CATALYST

BACKGROUND OF THE INVENTION

This invention relates to an improved process for dimerization of acrylonitrile to predominantly straight-chain $C_6$ dinitriles such as 1,4-dicyanobutene. More particularly, the invention relates to improvements in dimerization processes using organic phosphinite and/or phosphonite catalysts in the presence of a proton-donating solvent.

Dimerization of acrylonitrile to yield 1,4-dicyanobutenes by using organic phosphinite or phosphonite catalyst in the presence of a proton-donating solvent is described, for example, in U.S. Pat. Nos. 4,126,632; 4,102,915; and 4,138,428, the disclosure of said patents being incorporated herein by reference. According to the teachings of these patents the acrylonitrile is contacted with an organic phosphorus (III) compound which has at least one hydrocarbyl and at least one alkoxy or cycloalkoxy group attached to the phosphorus atom or atoms, the acrylonitrile being dissolved in an organic solvent capable of donating protons and the acrylonitrile and solvent being substantially dry.

Suitable organic phosphorus (III) compounds include those of the formulae:

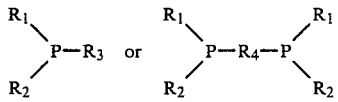

where $R_1$ is a hydrocarbyl group, $R_2$ is an alkoxy or cycloalkoxy group, $R_3$ is hydrocarbyl, alkoxy or cycloalkoxy group or other monovalent radical, and $R_4$ is a divalent hydrocarbyl, hydrocarbyloxy or other difunctional group. It is also possible that one or more groups $R_1$ to $R_3$ may form part of one or more ring systems. The hydrocarbyl groups may be aryl, alkyl, alkylaryl (polycyclic) or cycloalkyl.

The reaction is conducted in the presence of an organic solvent since in the absence of solvent rapid polymerization of the acrylonitrile occurs. Suitable solvents are proton donating solvents which are substantially unreactive in respect of addition to, or reaction with, the unsaturated linkage of the acrylonitrile or the products of acrylonitrile dimerization. Furthermore, the solvent must not react with the phosphorus compounds or catalytic intermediates to form inactive phosphorus species at such a rate as to seriously impair the dimerization reaction. For example, phenols have been found to be unsuitable in this respect.

Preferably, hydroxylic solvents, such as alcohols, are used, provided that they do not react adversely with the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range 5 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

It is further taught that in order to reduce the amount of hexamer and/or other oligomers or polymers (hereafter referred collectively as polymeric by-products or merely polymers) which may be co-produced with the desired dimeric products, it is often desirable to add an inert, non-hydroxylic co-solvent to the reaction mixture used in the process. The co-solvent is dried to a level which maintains the overall anhydrous state of the system.

Suitable non-hydroxylic organic co-solvents include hydrocarbons, for example, hexane, cyclohexane, toluene, and petroleum ethers; ethers, for example, tetrahydrofuran, diethyl ether and diisopropyl ether; and nitriles, for example, acetonitrile, propionitrile; and fluorobenzenes. The hydrocarbon co-solvents are generally preferred. To avoid ambiguity, inert non-hydroxylic co-solvents such as described will, hereafter, be consistently referred to as "co-solvents" to clearly distinguish them from proton donating solvents employed in the reaction mix.

The reaction is conducted in the substantial absence of water.

The unpurified product of reactions of this type contains residual dimerization catalyst. This residual catalyst causes further reaction which increases the proportion of undesired byproducts. Even after purification the product may contain very small amounts of catalyst which surprisingly, even at very low levels, cause continued degradation or poison catalysts used in subsequent hydrogenation processes used to convert the dicyanobutene to adiponitrile. Clearly, any reduction of such problems associated with residual catalyst would represent an advance in the art.

SUMMARY OF THE INVENTION

In accordance with the present invention, the dimerization reaction product described above is treated with an oxidizing agent to convert residual catalyst to an inactive form. The invention will be understood from the following description of the preferred embodiments.

DESCRIPTION OF THE PREFERRED EMBODIMENTS

In accordance with the present invention, the dimerization catalyst utilized is represented by the formula:

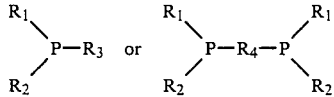

where $R_1$ is a hydrocarbyl group, $R_2$ is an alkoxy or cycloalkoxy group, $R_3$ is hydrocarbyl, alkoxy or cycloalkoxy group or other monovalent radical, and $R_4$ is a divalent hydrocarbyl, hydrocarbyloxy or other disfunctional group. It is also possible that one or more groups $R_1$ to $R_3$ may form part of one or more ring systems. The hydrocarbyl groups may be aryl, alkyl, alkylaryl (polycyclic) or cycloalkyl. A preferred catalyst within the scope of the formula is isopropyldiphenylphosphinite.

The amount of catalyst may be as taught in the foregoing references or, in accordance with a later discovered improvement (described in U.S. Pat. No. 4,841,087) the catalyst may constitute from 16% to 90% by weight of the reaction mixture with amounts of from 30 to 90% being preferred. The use of at least 70% catalyst is most preferred particularly when no co-solvent is present. Use of a co-solvent may be desired, particularly if lower proportions of catalyst in the range specified are utilized. In such case the volume of catalyst should be at least 28% of the volume of the co-solvent.

As previously mentioned, the reaction is conducted in the presence of a proton donating solvent. Suitable solvents are substantially unreactive in respect of addition to, or reaction with, the unsaturated linkage of the acrylonitrile or the products of acrylonitrile dimerization. Furthermore, the solvent must not react with the phosphorus compounds or catalytic intermediates to form inactive phosphorus species at such a rate as to seriously impair the dimerization reaction. For example, phenols have been found to be unsuitable in this respect.

Preferably, hydroxylic solvents, such as alcohols, are used provided that they do not react adversely with acrylonitrile, the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range of 5 to 20% by volume, calculated on the total volume of the reactants, but the optimum concentration will vary with the precise nature of the solvent and the catalyst compound. The reaction is conducted in the substantial absence of water.

Suitable co-solvents include non-hydroxylic organic solvents include hydrocarbons such as hexane, cyclohexane, benzene, toluene, and petroleum ethers; ethers, e.g., tetrahydrofuran, diethyl ether, diisopropyl ether; nitriles, e.g. acetonitrile, propionitrile; and fluorobenzenes. If any co-solvent is used, aromatic co-solvents are preferred.

As previously noted, the reaction is conducted in the absence of water. Thus, the acrylonitrile, proton-donating solvent and co-solvent, if employed, must be dried before use, otherwise the reaction may be completely inhibited. In particular, acrylonitrile, which commonly contains as much as 4000 ppm of water, even after distillation, must be rigorously dried. It is also preferable that hydroquinone stabilizers, which are present in acrylonitrile as supplied be removed. Any suitable drying technique may be used, provided that the final water level is sufficiently low. For example, acrylonitrile and hydroxylic solvents may be dried by being contacted with calcium hydride or a 3A or 4A molecular sieve. Azeotropic distillation may be employed.

The concentration of acrylonitrile in the solvent or solvent mixture generally should range from 5 to 75% by volume. The concentration of acrylonitrile is kept as high as possible in order to optimize throughput while maintaining useful yields and thus concentrations in the range 5 to 20% by volume are generally preferred.

The reaction temperature is commonly in the range 0° to 120° C.; but it is generally preferred to keep the temperature below 75° C. to minimize polymerization of the acrylonitrile and dimeric products. Preferably, the reaction temperature is in the range 20° to 70° C. It is noted that the reaction will proceed below 0° C., maintaining selectivity, but at a reduced rate.

The reaction may be carried out batchwise or continuously.

The dimeric products of the reaction are predominantly linear $C_6$ dinitriles, especially the 1,4-dicyanobutenes. Dimer selectivities greater than 90 wt % (calculated on total dimeric product) may be readily obtained and selectivities as high as 98% are obtainable. Actual yields are generally in the 85–95% range.

The desired products may be readily separated from the reaction mixture for example by fractional distillation or solvent extraction, but prior to separation and even after may contain residual catalyst. The term "residual catalyst" refers to the catalyst in the form it appears in the product which may vary somewhat from the previously given catalyst description.

An oxidizing agent is added to the crude or purified product containing the residual catalyst to oxidize and to render the catalyst inactive. The degree of oxidation required generally corresponds to that necessary to convert the P3+ of the active catalyst to a P5+ state. The oxidation can be accomplished by use of hydrogen peroxide solution or other oxidizing agents such as sulfur, potassium permanganate, sodium dichromote, nitric acid, ozone, chloromethyl ether, propionyl chloride, acetic anhydride, methyl acrylate plus water or the like.

The invention is further illustrated by the following examples. Although the examples employ isopropyl diphenyl phosphinite catalyst, the techniques described are generally applicable to the entire class of phosphinites (phosphinous acid esters) and phosphonites (phosphonous acid esters).

EXAMPLE I 0.013 parts of 30% $H_2O_2$ are added to 10 parts 1,4-butene containing 0.013 parts isopropyl diphenylphosphinite. Analysis of the mixture after 30 minutes shows 99.7% of the catalyst phosphorus has been converted to the plus 5 state.

EXAMPLE II 0.003 parts elemental sulfur are added to 10 parts dicyanobutene containing 0.011 parts isopropyl diphenylphosphinite. The phosphorus is quantitatively converted to the plus 5 state.

EXAMPLE III

The effect of catalyst phosphorus oxidation state on conversion of dicyanobutene to adiponitrile using a 3% paladium on carbon hydrogenation catalyst at 0.05% catalyst concentration; 10 atm hydrogen pressure and 120° C. is shown in the following table:

| Residual Dimerization Catalyst Phosphorus Oxidation State | % Residual Dimerization Catalyst | % Dicyanobutene Conversion |
|---|---|---|
| +3 | .1 | 4.6 |
| +3 | .05 | 4.4 |
| +3 | .01 | 12.7 |
| +5 | .3 | 99.8 |

The advantages of oxidation of the residual dimerization catalyst are thus evident.

What is claimed is:

1. A process for treating dicyanobutene containing residual dimerization catalyst selected from the group consisting of organic phosphorus (III) compounds represented by the formulae:

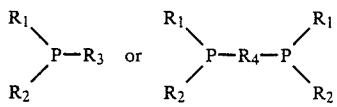

wherein $R_1$ is a hydrocarbyl group, $R_2$ is an alkoxy or cycloalkoxy group, $R_3$ is a hydrocarbyl, alkoxy or cycloalkoxy group, and $R_4$ is a divalent hydrocarbyl group, said process comprising contacting the residual catalyst with an oxidizing agent and converting the catalytic phosphorus to the plus 5 oxidation state.

2. The process of claim 1 wherein the catalyst is isopropyldiphenylphosphinite.

3. The process of claim 2 wherein the oxidizing agent is hydrogen peroxide.

4. The process of claim 2 wherein the oxidizing agent is sulfur.